United States Patent
Nishi et al.

(10) Patent No.: US 7,488,533 B2
(45) Date of Patent: *Feb. 10, 2009

(54) HIGHLY OIL ABSORBING AMORPHOUS SILICA PARTICLES

(75) Inventors: Shugo Nishi, Amagasaki (JP); Tatsuya Tokunaga, Okayama (JP)

(73) Assignee: DSL Japan Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/567,082

(22) PCT Filed: Jul. 30, 2004

(86) PCT No.: PCT/IB2004/002541

§ 371 (c)(1),
(2), (4) Date: Jul. 6, 2006

(87) PCT Pub. No.: WO2005/012176

PCT Pub. Date: Feb. 10, 2005

(65) Prior Publication Data

US 2007/0125269 A1    Jun. 7, 2007

(30) Foreign Application Priority Data

Aug. 5, 2003    (JP) .............................. 2003-286635

(51) Int. Cl.
*B32B 5/16*    (2006.01)
(52) U.S. Cl. ...................... 428/402; 423/335; 502/240; 502/407
(58) Field of Classification Search ................. 428/402; 423/334; 502/240, 407
See application file for complete search history.

(56) References Cited

U.S. PATENT DOCUMENTS

| | | | | |
|---|---|---|---|---|
| 4,330,519 A | * | 5/1982 | Takahashi et al. | ............ 423/335 |
| 5,964,937 A | * | 10/1999 | Stanier | ....................... 106/492 |
| 6,107,236 A | | 8/2000 | Pecoraro et al. | |
| 6,413,373 B1 | * | 7/2002 | Matsuda et al. | .......... 162/181.6 |

FOREIGN PATENT DOCUMENTS

| | | |
|---|---|---|
| JP | 58-076090 | 5/1983 |
| JP | 60-226826 | 11/1985 |
| JP | 05-124907 | 5/1993 |
| JP | 06-040714 | 2/1994 |
| JP | 11-157827 | 6/1999 |
| JP | 2002-226302 | 8/2002 |
| WO | 01/17901 | 3/2001 |
| WO | 2005/012176 | 2/2005 |

* cited by examiner

*Primary Examiner*—H. T Le
(74) *Attorney, Agent, or Firm*—Oblon, Spivak, McClelland, Maier & Neustadt, P.C.

(57) ABSTRACT

The present invention relates to amorphous silica particles having high oil absorbance capabilities, a process for their preparation and use thereof. The amorphous silica particles of the invention, wherein oil absorption measured by JISK 6217-4 is more than 400 ml/100 g can be obtained by baking at least 200 to 990° C.

15 Claims, 3 Drawing Sheets

Pores size distribution plot
D-H method (From absorption branch)

HIGHLY OIL ABSORBING AMORPHOUS SILICA PARTICLES

The present invention relates to amorphous silica particles having high oil absorbance capabilities, a process for their preparation and use thereof. More particularly, the present invention relates to amorphous silica particles with oil absorption of more than 400 ml/100 g, as measured by JISK 6217-4 (a carbon black for rubber—basic characteristics). The maximum value of $\Delta Vp/\Delta \log Rp$ (where Vp is the pore volume [mm$^3$/g] and Rp is the pore radius [nm]) is 250 mm$^3$/nm·g or more in the pore distribution curve obtained by the nitrogen adsorption isotherm method. The pore peak radius when $\Delta Vp/\Delta \log Rp$ value is at a maximum is 3 nm or more.

Silica is used for applications in a wide variety of fields including as a reinforcing filler for rubber, a carrier for agrochemicals, a chemical absorbent, a filler for making paper, a coating agent for special paper, a resin compounding agent, a matting agent for coating material, etc. in accordance with its physical and chemical characteristics which differ for every application requiring the availability of many types of silica.

Among these applications, high oil absorbance is required for the silica used in chemical adsorbing agents (adsorbing and oil absorbing), such as pharmaceuticals, agrochemicals and animal medicines, bathing agents, fillers for making paper, coating agents for the special paper, resin compounding agents, matting agents used for coating material or the like.

As an example of the amorphous silica particles having high oil absorbance, in Shiyou JP 58-88117A (1983), an amorphous silica having 400 to 600 m$^2$/g specific surface area and 340 to 380% DBP value has been indicated, wherein the amorphous silica was made by simultaneously adding a sodium silicate aqueous solution and sulfuric acid while applying a shearing force in a 6 to 7 pH, spraying and drying. In Kuhlmann et al. JP 2002-255534, amorphous silica particles having an oil absorption of 380 to 420 g/100 g (362 to 400 ml/100 g when the unit is converted to ml/100 g) have been indicated, wherein the amorphous silica particles were made by improving the filtrated cake water content and drying method (a spin flash dryer). Furthermore, in Hei JP H01-320215 (1989), the highly oil absorbing silica having the specific surface area of 150 to 350 m$^2$/g and the oil absorption of 300 to 400 ml/100 g has been indicated, wherein the silica was made by accelerating the growth and suitable agglomerations of particles while applying the shearing force to these particles at the aging time after a first stage reaction of a sodium silicate aqueous solution and a mineral acid, mixing the silica slurry with cationic surfactant, spraying and drying.

However, since chemical adsorbing agents (absorbing and oil absorbing), such as pharmaceuticals, agrochemicals, animal medicines, bathing agents, are required to have a more compact size and advanced functions, it is an important problem to increase the oil absorbing performance of the amorphous silica particles as the adsorbent. That is, increasing an active ingredient and compacting the size with the same chemical agent amount can be realized by increasing the adsorption of liquid chemical agent to the amorphous silica, so that the reduction of administrative costs or logistics costs and improvement of a handling of consumers can be expected. In the above-mentioned silica particles, all of these silica particles have oil absorptions of 400 ml/100 g or less, but the further improvement has been desired from the viewpoint of the highly oil absorbing silica.

Moreover, the amorphous silica, especially the sedimenting silica, has high bulkiness and requires much labor for mixing with the paper or the coating material as a filler for making paper, a coating agent for special paper or a matting agent for a coating material Furthermore, the mixing amount is also limited thus requiring a solution for these problems.

It was an object of the present invention, therefore, to provide new silica capable to solve at least some of the aforementioned problems. The intention is likewise to provide a process for the preparation of the silica of the invention.

For solving the above problems, wholehearted investigations were carried out and, as the result, it was discovered that the amorphous silica particles having the oil absorption of 400 ml/100 g or more could be made by making amorphous silica particles having the oil absorption of 340 ml/100 g or more and baking these silica particles at 200 to 990° C.

The present invention therefore provides amorphous silica and a process for their manufacture as defined in the Claims and the description of the present invention.

The present invention particularly provides amorphous silica particles, wherein the oil absorption measured by JISK 6217-4 (a carbon black for rubber—basic characteristics) is more than 400 ml/100 g, the maximum value of $\Delta Vp/\Delta \log Rp$ (where Vp is the pore volume [mm$^3$/g] and Rp is the pore radius [nm]) is 250 mm$^3$/nm·g or more in the pore distribution curve obtained by the nitrogen adsorption isotherm method, and the pore peak radius when the $\Delta Vp/\Delta \log Rp$ value is maximum is 3 nm or more.

The present invention also provides a process for preparing amorphous silica, wherein silica particles are baked at 200-990° C. preferably 200-900° C.

The present invention also provides the use of amorphous silica according to the invention for example as matting agent, adsorbent (carrier for pharmaceuticals or agrochemicals), extender or filler of various rubbers or the like.

The present invention in addition provides matting agents and adsorbents for pharmaceuticals and agrochemicals comprising the amorphous silica particles of the invention.

Amorphous silica particles are invented, wherein the oil absorption measured by JISK 6217-4 (the carbon black for rubber—basic characteristics) is more than 400 ml/100 g, the maximum value of $\Delta Vp/\Delta \log Rp$ (where Vp is the pore volume [mm$^3$/g] and Rp is the pore radius [nm]) is 250 mm$^3$/nm·g or more in the pore distribution curve obtained by the nitrogen adsorption isotherm method, and pore peak radius when the $\Delta Vp/\Delta \log Rp$ value is maximum is 3 nm or more. Since these amorphous silica particles have high oil absorption, it is possible to increase the adsorption effect of pharmaceuticals or agrochemicals or the matting effect with a small amount when these particles are used as the adsorbent of the pharmaceutical or agrochemical or the matting agent for coating material or the like.

Although an alkaline silicate being the raw material of these amorphous silica particles of the present invention is not limited especially. The following can be used, that is, sodium silicate or potassium silicate, such as water glass standardized according to JIS as an industrial product, an alkali silicate made by reacting a readily reactive silica with a hydroxide solution of an alkaline metal, or the like, where the reactive silica is recovered from a clayey raw material, such as acidic clay or the like. When the above alkali silicate is used as an aqueous solution, the silica concentration of the aqueous solution is not limited especially but is generally 1 to 30% by weight, preferably 2 to 20% by weight, and more preferably 2.5 to 10% by weight. When the concentration is less than 1% by weight, the production efficiency becomes low and the economical disadvantageousness increases. When the concentration is more than 30% by weight, the viscosity of the reaction solution becomes high, the reaction looses uniformity, and thus the handling of silica slurry after the reaction becomes very difficult. Furthermore, the mol ratio of $SiO_2$: $M_2O$, where M is an alkaline metal, is 2:1 to 4:1 generally, and preferably 2.5:1 to 3.5:1. These mole ratios are called No. 2 diatom, No. 3 diatom, No. 4 diatom, or the like. In general, the No. 3 diatom is preferably used for its cost effectiveness.

As the mineral acid used for neutralization in making the amorphous silica particles, carbonated water, carbonated gas, acetic acid, a Lewis acid, hydrochloric acid, sulfuric acid, nitric acid or the like can be used although it is not limited especially. Particularly, the sulfuric acid is preferably used from the viewpoint equipment and economy. The concentration of the mineral acid aqueous solution is generally 5 to 75% by weight, preferably 10 to 60% by weight and more preferably 10 to 45% by weight.

As the method for making the amorphous silica particles of the present invention, although it is not limited especially, the commonly known method for making the conventional amorphous silica can be used, wherein an aqueous solution of alkali metal silicate is neutralized with an acid.

For example, a gel method, a precipitating method, or a combination of these methods can be used. When these methods are used together, it is necessary to control the growths and agglomerations of the amorphous silica particles, which is used as a nucleus generated by the first stage reaction and the silica particles aged after this generation. That is, it is necessary to decide the conditions for making the silica by considering the particle size or the pore size of the silica particles used as the nucleus, and the particle size and the pore size of the silica particles after aging. As a method for the neutralization by contacting both raw materials, although it is not limited especially, there are two methods, that is, the method where one of the raw materials is added to the aqueous solution of another raw material while stirring, and the method where both solutions of raw materials are contacted simultaneously under fixed conditions. Some examples of making the silica are shown in the following.

In one preferred embodiment of the invention, the amorphous silica particles of the present invention were prepared by a process, wherein first, the alkaline silicate aqueous solution and a mineral acid aqueous solution are neutralized in pH of 2 to 10 to directly make silica slurry having 2 to 10% by weight silica concentration. Or silica slurry is made by the neutralization of the alkaline silicate aqueous solution and the mineral acid aqueous solution having 5 to 30% by weight silica concentration by weight by leaving for 30 minutes or more in general. The neutralization temperature is preferably 50° C. or less to form silica having a uniform texture, although it is not limited especially. Furthermore, the neutralization may be carried out while applying the shearing force by a wet type pulverizer or the like according to need.

After the obtained silica is washed, a heating treatment may be carried out for a moisture adjustment and a pore adjustment according to need. The temperature of the heating treatment is generally within the range from 40 to 200° C., preferably from 70 to 190° C., and more preferably from 100 to 170° C. The heating treatment can be carried out, for example, in an autoclave, and the time for the heating treatment may be adjusted according to the pore peak radius. The time is generally 5 minutes to 30 hours, preferably 30 minutes to 20 hours, and more preferably 1 hour to 15 hours.

After that, the silica slurry may be wet-pulverized so as to have an average particle size of 500 μm or less, preferably 2 to 200 μm, and more preferably 3 to 100 μm, according to need. The silica slurry may be coarsely pulverized before the heating treatment or during the heating treatment according to the case, but the filtration efficiency is insufficient, and the silica slurry may be agglomerated again when it is compressed at the filtration, so that the silica slurry has to be repulverized after the filtration in this case.

As for the wet type pulverization, a commonly known method can be applied. For example, a bead mill, such as a dyno-mill made by WAB Company, a high shear mixer made by Silverson Company, a homo mixer or a line mill made by Tokushukika Company or the like can be suitable. If a high speed shearing force is possible, other wet type pulverizers can also be used.

The temperature at the time of the wet type pulverization is not particularly limited, but when the pulverization is carried out during the reaction or the heating treatment, it can be carried out under the same temperature. However, when the pulverization is carried out after ending the pore size adjustment, the temperature of the slurry must be less than 50° C. to decrease the agglomeration between particles.

After that, the predetermined amorphous silica can be obtained by filtrating the silica slurry and drying. As a drying method, the commonly known method such as by air-drying or spray-drying can be used. In general, when a highly oil absorbing silica is wanted, a spray dryer or a spin flush dryer capable of drying for a short time is preferably used. In the case of the spray dryer, two methods are used generally for finely atomizing the slurry, that is, one is using a spray disc (atomizer), the other is using a two-fluid nozzle, but it is not particularly used in the present invention. In addition, when the slurry is dried by the spray dryer, almost spherical solid particles can be made. The temperature of the hot air of the spray dryer is 80 to 600° C., preferably 100 to 500° C., and more preferably 120 to 450° C. In order to improve the oil absorption, it is more advantageous that the temperature of the hot air is high, however, when the temperature is 600° C. or more, production cost of the dryer becomes high in order to have heat resistance and a special facility design. On the other hand, when the temperature is 100° C. or less, the production efficiency is insufficient. In particular, it can be optimized with the relationship between the performance of the spray dryer and the spraying speed, but the above-mentioned temperature range is preferable in general. Furthermore, the moisture can be easily removed from the surface of the particles in an aqueous phase and shrinkage of the amorphous silica particles during the drying process can be effectively controlled by adding a cationic surfactant, such as alkyldimethylbenzyl-ammonium chloride or the like, to the slurry before drying according to necessity, so that the oil absorption can be increased.

By the above-mentioned production method, the amorphous silica particles having an oil absorption of 340 ml/100 g or more can be obtained. There is a correlation between the oil absorption and moisture content in general, and the oil absorption becomes high as decreasing the moisture content in the same amorphous silica. However, only removing the moisture is not sufficient for increasing the oil absorption. After a wholehearted investigation, it was found that the oil absorption was remarkably increased by baking the amorphous silica particles made in this way, and then, the amorphous silica particles having the oil absorption of more than 400 ml/100 g could be made. The baking temperature is 200 to 990° C., preferably 200 to 950° C., more preferably 200 to 900° C., and even more preferably 300 to 900° C. Further, the baking time is preferably 1 minute to 10 hours, and more preferably 10 minutes to 5 hours, although it changes with the baking temperature. The reason why the oil absorption is remarkably increased by baking is not clear. However, it is supposed that the pore is agglomerated by baking while keeping the basic structure of the amorphous silica particles and the comparatively large size pore increases. As equipment for baking, the conventional equipment, such as a baking furnace, a rotary kiln or the like, can be used.

In a second preferred embodiment of the invention, the amorphous silica particles of the present invention were prepared by a process, wherein the alkaline silicate aqueous solution and the mineral acid aqueous solution are neutralized in a pH of 5 to 10 to give the silica slurry a 2 to 10% by weight silica concentration. In this case, types, concentrations and neutralization method of the alkaline silicate aqueous solution and mineral acid aqueous solution are the same as the above-mentioned method. The neutralization temperature is preferably 30° C. or more, more preferably 50° C. or more, and furthermore preferably 70° C. or more, although it is not limited especially. When the temperature is less than 30° C., the reaction rate is slow, and thus it is not efficient. Further, the neutralization can be carried out while applying the shearing force using the wet type pulverizer mentioned above or the like, according to need. After that, the generated silica slurry can be aged according to its physical properties. The conditions of a neutralization degree, the neutralization temperature and the concentration of the sodium silicate aqueous solution in the method of the present invention are complexly correlated with aging conditions, and thus the conditions cannot be easily decided overall.

As for the general aging conditions, the pH is 6 to 12, the temperature is 50 to 130° C., and the reaction time is 3 to 180 minutes. Preferably, the pH is 7 to 11.5, the temperature is 60 to 110° C. and the reaction time is 3 to 165 minutes. More preferably, the pH is 8 to 11, the temperature is 65 to 100° C. and the reaction time is 5 to 150 minutes. Especially preferably, the pH is 8 to 11, the temperature is 70 to 100° C. and the reaction time is 5 to 140 minutes. Further, the silica can be aged while applying a shearing force using the wet type pulverizer mentioned above or the like, according to need.

Further, as the second stage reaction, the mineral acid can be added simultaneously to the slurry made by the first stage reaction while adding the sodium silicate aqueous solution. In this case, although the concentration of the mineral acid added for the second stage reaction is within the same concentration range as that of the first stage reaction, it is preferable that the concentration of the sodium silicate aqueous solution is within the same range as that of the first stage reaction or lower. Further, the pH at the second stage reaction is preferably fixed generally at 4 to 10, preferably at 6 to 10, and more preferably at 7 to 9.5.

After that, the pH of the obtained silica slurry is adjusted to 4 or less, preferably 3 or less, and then the second stage reaction is stopped. According to need, the slurry is diluted with water, and the coarse particles are separated by a rotary pump and a hydrocyclone if necessary, and after that, the slurry is filtrated and washed. This filtration and washing can be carried out by using a commonly known instrument, such as a filter press, a rotary filter or the like.

The filter cake obtained in this way is pulverized to have the suitable size, and is slurried again by carrying out the air-drying or stirring while adding water. After that, the slurry solution can be dried by the spray dryer, the nozzle dryer or the like. The specified particle size distribution can be adjusted by using the dryer. This distribution can be adjusted as per the kind of dryer and the selection of an applied spraying pressure. In order to make the especially highly oil absorbing silica, the drying is preferably carried out by the spray dryer. When the spray dryer is used, the drying can be carried out under the same conditions as the above-mentioned conditions.

By the above-mentioned making method, the amorphous silica particles having the oil absorption of 340 ml/100 g or more can be obtained. The amorphous silica particles having the oil absorption of more than 400 ml/100 g can be made by baking the obtained amorphous silica particles. The baking temperature is 200 to 990° C., preferably 200 to 950° C., more preferably 200 to 900° C., and even more preferably 300 to 900° C. especially preferred 400 to 900° C. Further, the baking time is preferably 1 minute to 10 hours, and more preferably 10 minutes to 5 hours, although it changes with the baking temperature.

Moreover, as for the pH of the obtained silica, the suitable pH is changed according to the application. More particularly, when the silica is used as the adsorbent for pharmaceuticals or agrochemicals, the pH influences the stability of a pharmaceutical active ingredient, such as vitamin E or the like, or an agrochemical active ingredient, such as an organophosphorus agent or the like, and is very important. The pH of the amorphous silica particles when used as the adsorbent of pharmaceuticals or agrochemicals is generally 3 to 10, preferably 4 to 9, and more preferably 5 to 8. However, the pharmaceuticals or agrochemicals adsorbed in the silica can be stabilized by applying the adjusted silica, according to the each case, that is, applying the silica adjusted to acid in the case of the compound being stable in acid, and applying the silica adjusted to alkaline in the case of the compound being stable in alkaline. As the method for adjusting pH, there are two methods, that is, a method adjusting the pH of the silica slurry before drying, and a method adjusting the pH by adding ammonia gas or the like after drying.

The amorphous silica of the invention may be obtained by a method described above and are characterized in that their oil absorption measured by JISK 6217-4 (a carbon black for rubber—basic characteristics) is more than 400 ml/100 g, the maximum value of $\Delta Vp/\Delta \log Rp$ (where Vp is the pore volume [$mm^3/g$] and Rp is the pore radius [nm]) is 250 $mm^3/nm \cdot g$ or more in the pore distribution curve obtained by the nitrogen adsorption isotherm method, and pore peak radius when the $\Delta Vp/\Delta \log Rp$ value is maximum is 3 nm or more.

In the pore distribution curve obtained by the nitrogen adsorption isotherm method, the maximum value of $\Delta Vp/\Delta \log Rp$ (where Vp is the pore volume [$mm^3/g$] and Rp is the pore radius [nm]) is 250 $mm^3/nm \cdot g$ or more, preferably 500 $mm^3/nm \cdot g$ or more, more preferably 1000 $mm^3/nm \cdot g$ or more, and even more preferably 1500 $mm^3/nm \cdot g$ or more, most preferably 2000 $mm^3/nm \cdot g$ or more, especially preferred 2500 $mm^3/nm \cdot g$ or more. When the maximum value of $\Delta Vp/\Delta \log Rp$ (where Vp is the pore volume [$mm^3/g$] and Rp is the pore radius [nm]) is less than 250 $mm^3/nm \cdot g$, there is an remarkably high open structure so that the effect of increasing the oil absorption by baking is low.

Moreover, the pore peak radius is 3 nm or more, preferably 10 nm or more, more preferably 15 nm or more, and even more preferably 20 nm or more, most preferably 25 nm or more, especially preferred 30 nm or more. When the pore peak radius is less than 3 nm, the particle size is small, so that the pore may disappear during baking. Further, the maximum of the pore peak radius is 100 nm due to the measurement.

The amorphous silica particles of the invention may exhibit an oil absorption measured by, JISK 6217-4 (a Brabender method) in which the oil absorption of DBP (Dibutylphthalat) is determined. The oil absorption of the amorphous silica of the present invention (a dropping rate is 4 ml/minute) is more than 400 ml or more per 100 g of the amorphous silica particles (400 ml/100 g), preferably 405 ml (405 ml/100 g) or more, and more preferably 410 ml (410 ml/100 g) or more.

The BET specific surface area is one of the basic properties of amorphous silica, and influences the oil absorption, transparency of the particles and handling of the amorphous silica particles. The amorphous silica of the invention may exhibit a BET specific surface area in the range of 50 to 800 m$^2$/g, preferably 100 to 700 m$^2$/g, more preferably 140 to 650 m$^2$/g, and even more preferably 150 to 600 m$^2$/g. When the BET specific surface area is less than 50 m$^2$/g, the matting effect may be decreased since there are little amounts of the large size pore to decrease the transparency of the amorphous silica particles. On the other hand, when the BET specific surface area is more than 800 m$^2$/g, the pore size becomes very small, so that the oil absorption performance is decreased although the transparency is increased.

The amorphous silica obtained by the methods described above can be merchandised as is, but the particle size of the silica can be adjusted according to the application. The particle size can be adjusted by carrying out a dry classification after pulverizing. As the pulverizer, it is not especially limited, and all commonly known pulverizer can be used, for example, an air current impact type pulverizer, such as Jet-O-Mizer or the like, a hammer mill, such as an atomizer or the like, a pin mill, such as a centrifugal classifier or the like, can be used. As a classifier, although it is not especially limited, a dry classifier, such as a microplex, a turbo classifier or the like, is suitable when a precise classification is required. On the other hand, the silica slurry after washing can be dried after classifying by a wet classifier, such as a precipitation classifier, a hydraulic classifier, a mechanical classifier, a centrifugal classifier or the like. In the present invention, the spray drying method is effective.

More particularly, when the silica is used as the filler for an ink jet recording paper, the matting agent, an antiblocking agent or the like, the adjustment of the particle size is important, as indicated in many patents and documents.

The amorphous silica of the invention may therefore exhibit a median size which is based on volume and the average particle size within a 0.5 to 40 μm range, preferably 0.75 to 30 μm, more preferably 1 to 25 μm, and even more preferably 1 to 20 μm, most preferably 1 to 15 μm, especially preferred 1 to 9 μm.

The bulk density is a very important physical property in the handling of amorphous silica particles. The silica of the invention may therefore be characterized by a bulk density in the range of 20 to 200 g/l, preferably 30 to 150 g/l, more preferably 40 to 125 g/l, and furthermore preferably 50 to 120 g/l. When the bulk density is less than 20 g/l, the handling is difficult since the bulk becomes very high, and when the bulk density is more than 200 g/l, the oil absorption may be decreased.

The aforementioned physical and chemical properties of the amorphous silica of the invention may be combined independently. Particularly preferred combinations are described in the following paragraphs.

The physical properties of the amorphous silica particles of the present invention are preferably as follows, that is, the oil absorption measured by JISK 6217-4 (the carbon black for rubber—basic characteristics) is more than 400 ml/100 g, the maximum value of $\Delta Vp/\Delta \log Rp$ (where Vp is the pore volume [mm$^3$/g] and Rp is the pore radius [nm]) is 250 mm$^3$/nm·g or more in the pore distribution curve obtained by the nitrogen adsorption isotherm method, and the pore peak radius is 3 nm or more. More preferably, the oil absorption is 405 ml/100 g, the maximum value of $\Delta Vp/\Delta \log Rp$ is 500 mm$^3$/nm·g or more, and the pore peak radius is 10 nm or more. Even more preferably, the oil absorption is 410 ml/100 g, the maximum value of $\Delta Vp/\Delta \log Rp$ is 1000 mm$^3$/nm·g or more, and the pore peak radius is 15 nm or more.

More particularly, the physical properties of the amorphous silica particles of the present invention are as follows, that is, the oil absorption measured by JISK 6217-4 (the carbon black for rubber—basic characteristics) is more than 400 ml/100 g, the maximum value of $\Delta Vp/\Delta \log Rp$ (where Vp is the pore volume [mm$^3$/g] and Rp is the pore radius [nm]) is 250 mm$^3$/nm·g or more, the pore peak radius is 3 nm or more, the BET specific surface area is 50 to 800 m$^2$/g, the average particle size is 0.5 to 40 μm, and the bulk density is 20 to 200 g/l. Preferably, the oil absorption is 405 ml/100 g or more, the maximum value of $\Delta Vp/\Delta \log Rp$ is 500 mm$^3$/nm·g or more, the pore peak radius is 10 nm or more, the BET specific surface area is 100 to 700 m$^2$/g, the average particle size is 0.75 to 30 μm, and the bulk density is 30 to 150 g/l. More preferably, the oil absorption is 410 ml/100 g or more, the maximum value of $\Delta Vp/\Delta \log Rp$ is 1000 mm$^3$/nm·g or more, the pore peak radius is 15 nm or more, the BET specific surface area is 140 to 650 m$^2$/g, the average particle size is 1 to 25 μm, and the bulk density is 40 to 125 g/l. Even more preferably, the oil absorption is 410 ml/100 g or more, the maximum value of $\Delta Vp/\Delta \log Rp$ is 1500 mm$^3$/nm·g or more, the pore peak radius is 20 nm or more, the BET specific surface area is 150 to 600 m$^2$/g, the average particle size is 1 to 20 μm, and the bulk density is 50 to 100 g/l.

The highly oil absorbing amorphous silica particles were invented. As for the amorphous silica particles of the present invention, since it has a high absorbency, a large amount of liquids, such as agrochemicals, feed, cosmetics, perfume, detergent, liquid vitamin (especially vitamin E) or the like can be powdered with a small amount of the amorphous silica powder. Since the silica particles of the present invention have high oil absorbency, they can be used as matting agent for coating materials or the like, as extender of agrochemicals, or as reinforcing agent of various rubbers.

The main application of the amorphous silica particles of the present invention is therefore the use as matting agent, carrier respectively adsorbent of liquids and as reinforcing agent for various rubbers.

The silica of the invention can be used in particular in the field of pharmaceuticals, agrochemicals and bathing agents, as powdering of the liquid component of vitamin A, vitamin E, a pyrethroid, an organophosphorus agent, a herbal medicine extracting component or the like, the extender, the caking preventing agent, the fluidity improving agent, or a pulverizing auxiliary. For example, when vitamin E is powdered, vitamin E of preferably 2.4 times or more by a weight ratio, more preferably 2.6 times or more, and even more preferably 2.8 times or more can be adsorbed in 100 g of the amorphous silica particles of the present invention. Further, the silica particles can be used as a stabilizing agent by adjusting the pH of the silica according to the stability of an active ingredient. In the agrochemicals field, the silica particles can be used as the precipitation preventing agent in each floatable agent, and a validity-strengthening agent according to cases, in addition to the usage in the above-mentioned pharmaceuticals and bathing agent.

Moreover, the silica particles are used as powdering, the fluidity improving agent and the caking preventing agent of the surfactant, the filler of a battery separator, the auxiliary of adhesives, a thickening agent and auxiliary in toothpaste, a base material for adjusting the mol ratio of sodium silicate, powdering of chemicals for rubber, a powdery fluidity improving agent, a caking preventing agent or a heat-insulating material of refractories, a humidity modifier as itself or a coating agent for walls, or a jet-flowability improving agent, caking preventing agent and texture improving agent in food, or the like.

Furthermore, the amorphous silica particles of the present invention can be used as a chromatography carrier, a cosmetic base, a coating material for electronic parts, a moisture absorbent for electronic parts, and other applications of the amorphous silica particles.

When the amorphous silica particles of the present invention are used as a carrier for the agrochemicals, it can be applied to all commonly known dosage forms by mixing with an agrochemical technical product, and is not especially limited. In addition, in the field where a conventional precipitating silica is used, the amorphous silica particles can be used satisfactorily. For example, the following formulations can be used, that is, a fine powder-like formulation, such as powder granules, wettable granules or the like, a powder-like formulation, such as granules, powdery granules, granular wettable granules or the like, a solid formulation such as tablets or the like, a uniform solution-like formulation, such as a solution, an oil solution, an emulsion, a micro emulsion or the like, or an emulsification or suspension-like formulation, such as suspension in water, suspension in oil, emulsion in water, emulsion in oil, microcapsule or the like. Each formulation can be made by commonly known composites and production methods.

For example, in the case of the solid formulation, when the agrochemical technical product is a solid and the other auxiliary component is a solid, the silica particles can be used as, for example, the pulverization auxiliary, the fluidity improving agent, a powder explosion decreasing agent, a caking preventing agent or the like. When the agrochemical technical product is liquid or semi-solid, or contains a solvent or the like in the formulation, the silica particles can be used as, for example, the adsorbent of the agrochemical technical product, the solvent or the like. Moreover, in the case of the liquid formulation, the silica particles can be used as, for example, the viscosity modifier for preventing the precipitation, or the fluidity improving agent of the solid component mixed in the liquid. Furthermore, in the case of mixing the solid component after the pulverization, the silica particles can be used as, for example, the pulverization auxiliary, the fluidity improving agent, the powder explosion decreasing agent or the like.

A further particular preferred use of the silica of the invention is as matting agent. The amorphous silica particles itself can be blended with the commonly known coating material to become a matte coating composition. As the coating material, the coating materials commonly known and used can be used, that is, for example, an oil coating material, a nitrocellulose coating material, alkyd resin coating material, an amino alkyd coating material, a vinyl resin coating material, an acrylate resin coating material, an epoxy resin coating material, a polyester resin coating material, a chlorinated rubber-base coating material or the like. Further, in addition to these materials, the coating material containing one or more kinds of following resins can be used, that is, a rosin, an estergum, a pentaresin, a coumarone indene resin, a phenol-based resin, a modified phenol-based resin, a maleic-based resin, an alkyd-based resin, an amino-based resin, a vinyl-based resin, a petroleum resin, epoxy-based resin, a polyester-based resin, a styrene-based resin, an alkyl-based resin, a silicone-base resin, a rubber-based resin, a chloride-based resin, an urethane-based resin, a polyamide-based resin, polyimide-based resin, a fluorine-based resin, a nature or synthetic Japanese lacquer or the like.

Further, as for the using coating material, although the solution-type coating material, a water-based coating material, an ultraviolet curable coating material, a powder coating material or the like can be used arbitrarily, the present invention is especially suitable for a solution type coating material and a water-base coating material.

As an organic solvent of the solution type coating material, one or more of the following solvents can be used, that is, an aromatic hydrocarbon-based solvent, such as toluene, xylene or the like; an aliphatic hydrocarbon-based solvent, such as n-heptane, n-hexane, isobar or the like, an alicyclic hydrocarbon-based solvent, such as cyclohexane or the like; a ketone-based solvent, such as acetone, methylethyl ketone, methylisobutyl ketone, cyclohexanone or the like; an alcohol-based solvent, such as ethanol, propanol, butanol, diacetone alcohol or the like; an ether-based solvent, such as tetrahydrofuran, dioxane or the like; a Cellosolve-based solvent, such as ethyl Cellosolve, butyl Cellosolve or the like; an ester-based solvent, such as ethyl acetate, butyl acetate or the like; an aprotic polar solvent, such as dimethylformamide, dimethylacetamide, dimethylsulfoxide or the like. A resin content concentration in a raw material solution is generally within the range from 5 to 70% by weight, suitably from 10 to 60% by weight.

Further, as the water-based coating material, a self-emulsifying or a surfactant-emulsifying coating material is used, other than the water-based solution type coating material. As a resin of the water-based coating material, the following resins being water-solubilized or self-emulsified to the water-based solvent can be used, that is, an alkyd resin, a polyester resin, an acrylic resin, an epoxy resin, or a mixture of two or more kinds of these resins. In the self-emulsifying resin, the self-emulsifying property is given by neutralizing a carboxyl group with ammonias or amines or quaternizing the contained amines. Further, various latex resins are also used. The resin content concentration is generally within the range from 10 to 70% by weight, especially suitable from 20 to 60% by weight.

As the ultraviolet (UV) curable coating material, the following resins can be used, that is, a high solid resin, for example, an UV curable acrylic resin, an UV curable epoxy resin, an UV curable vinyl urethane resin, an UV curable acrylic urethane resin, or a UV curable polyester resin. These resins are used independently or by mixing two or more.

As the powder coating material, the following can be used, that is, a thermoplastic resin, such as polyamide, polyester, an acrylic resin, an olefine resin, a cellulosic derivative, polyether, a vinyl chloride resin or the like, an epoxy resin, an epoxy/novolak resin, an isocyanate or epoxy curable polyester resin or the like.

As for the amorphous silica particles used for the present invention, the surface of the silica particles can be coated or surface-treated with an inorganic oxide, such as titanium oxide, silicon oxide, zirconium oxide, zinc oxide, barium oxide, magnesium oxide, or calcium oxide, or a coupling agent such as a silane-based, titanium-based or zirconium-based coupling agent.

Moreover, as for the amorphous silica of the present invention, the coating of waxes can be carried out with the request material using a metallic soap, a resin acid soap or various resins. More particularly, the wax treatment by an olefin-based resin wax, such as a polyethylene wax, an oxidation polyethylene wax or an acid-modified polyethylene wax, an animal and vegetable wax, a mineral-based wax or the like is effective for increasing the matting effect or improving scratch resistance. The coating treatment can be carried out easily by adding an aqueous emulsion of the wax to the cake of the washed amorphous silica and mixing. The weight ratio of the surface-treated wax to the amorphous silica is 1 to 20%, where the amorphous silica is 100%, preferably the 3 to 15%.

In the present invention, the amorphous silica particles can be not only independently used as matting agent, but also for blending the coating material with other filler or pigment. As the inorganic component blended with the coating material, the following can be used, that is, alumina, attapulgite, kaolin, carbon black, graphite, fine powdered silicic acid, calcium silicate, diatomaceous earth, magnesium oxide, magnesium hydroxide, aluminum hydroxide, slate powder, sericite, flint, calcium carbonate, talc, feldspar powder, molybdenum disulfide, barite, vermiculite, whiteing, mica, pyrophyllite clay, gypsum, silicon carbide, zircon, glass bead, shirasu balloon, asbestos, glass fiber, carbon fiber, rock wool, slag wool, boron whisker, stainless steel fiber, titanium white, zinc white, red oxide, iron black, yellow iron oxide, zeolite, hydrotalcite, lithium, aluminum, carbonate, titan yellow, chrome oxide green, ultramarine blue, Prussian blue, or the like.

Also preferred is the use of the amorphous silica particles of the present invention as the filler for blending a thermoplastic resin, a thermosetting resin or various rubbers, and especially, as an antiblocking agent. As the thermoplastic resin where the amorphous silica is blended as the antiblocking agent, an olefin-based resin is suitable, and especially, the following resins can be used, that is, polyethylene, isotactic polypropylene or syndiotacic polypropylenic, which have low, middle or high density, a polypropylene-based polymer being a copolymer of these ethylene and □-olefin, linear low density polyethylene, an ethylene-propylene copolymer, polybutene-1, ethylene-butene-1 copolymer, a propylene-butene-1 copolymer, an ethylene-propylene-butene-1 copolymer, an ethylene-vinyl acetate copolymer, an ion cross-linking olefin copolymer (ionomer), ethylene-acrylic ester coplymer, or the like. These resins can be used independently or in a blended-state by mixing two or more. The amorphous silica particles of the present invention are useful as an antiblocking agent of the olefin-based resin film made by using a metallocene catalyst, and can solve the coloration tendency of the conventional antiblocking agent.

Of course, the antiblocking agent of the present invention can be blended with other commonly known resin films. For example, the agent can be blended with polyamide, such as nylon 6, nylon 6-6, nylon 6-10, nylon 11, nylon 12 or the like, thermoplastic polyester, such as polyethylene terephthalate, polybutylene terephthalate or the like, polycarbonate, polysulfone, a vinyl chloride resin, a vinylidene chloride resin, a fluoridation vinyl resin, or the like.

When the application is the antiblocking agent, the blending ratio of the silica particles to thermoplastic resin, where the thermoplastic resin is 100%, is 0.005 to 10% by weight, preferably 0.05 to 3.0% by weight, and more preferably 0.1 to 1.0% by weight.

The amorphous silica particles of the present invention can be blended with the thermoplastic resin, various rubbers or thermosetting resin, as the filler.

As an elastomer polymer for rubber, for example, the following can be used, that is, nitrile-butadiene rubber (NBR), styrene butadiene rubber (SBR), chloroprene rubber (CR), polybutadiene (BR), polyisoprene (IIB), butyl rubber, natural rubber, ethylene propylene rubber (EPR), ethylene-propylene-diene rubber (EPDM), polyurethane, silicone rubber, acrylic rubber or the like, and further, the thermoplastic elestomer, such as a styrene-butadiene-styrene block copolymer, a styrene-isoprene-styrene block copolymer, a hydrogenation styrene-butadiene-styrene block copolymer, a hydrogenated styrene-isoprene-styrene block copolymer or the like.

As the thermosetting resin, the following resins can be used, that is, a phenol formaldehyde resin, a furan-formaldehyde resin, a xylene-formaldehyde resin, a ketone-formaldehyde resin, a urea-formaldehyde resin, a melamine-formaldehyde resin, an alkyd resin, a unsaturated polyester resin, an epoxy resin, a bismaleimide resin, a triallyl cyanurate resin, a thermosetting acrylic resin, a silicone resin, or a mixed resin of two or more of these resins.

When the amorphous silica particles are used as reinforcing agent, the silica particles can be blended with the thermosetting resin or elastomer within a range of 0.5 to 20% by weight, and preferably 2 to 10% by weight, where the thermosetting resin or elastomer is 100%.

Beside the above mentioned applications, the amorphous silica of the invention may be used as a defoaming effect increasing agent for a defoaming material, a fluidity improving agent or a caking preventing agent of a powder fire extinguishing agent, a storage stability improving agent of the fluidity improving agent or caking prevention of various powders or the like, a filler of printing ink, a blur prevention agent of a newspaper ink, a purification adsorbent, a filter auxiliary agent for adsorbing proteins such as beer or the like, the powdering of the liquid component in feed, a milk extender, a fat conc, a milk powder, urea for drinks, a caking preventing agent of a caking substance such as a natural mixture or the like, an adsorbent of oil or fat of a feed for fish, a sintering preventing agent, a blocking preventing agent for the plastic industry or a blow film, such as polyethylene, polypropylene, PVC, HTV silicone rubber, a melamine resin, a phenol resin, a phenol-melamine resin or the like, a plate out preventing agent, a filler for polychloroprene rubber, thermoplastic rubber, silicone rubber or above-mentioned resins, an improving agent of mechanical characteristics of these flooring materials, an improving agent of measurement characteristics or caking preventing agent of these molded compounds, an adhesive auxiliary, a wear resistant improving agent, an improving agent of heat resistance/dimensional stability of TR crepe sole, a caking preventing agent of a foamed polystyrene granule preliminarily molded material, and a nucleating agent of a pattern constituting of a secondary molded film of styrene foam. Moreover, in a lacquer, varnish paint and mixture of these paints, the amorphous silica particles of the present invention are used as a partial replacement of titanium oxide or a white pigment in emulsion paint or ornament paint, a matting agent of a coating material, ink or the like, a precipitation preventing agent, a viscosity modifier, and a caking preventing agent.

Furthermore, in the papermaking industry, the amorphous silica particles are useful as a partial replacement for titanium dioxide, the improving agent of a contrast for blue printing paper, a coating agent for paper, and especially, a filler for ink jet recording paper and a strike-through preventing agent for papermaking.

EXAMPLES

Hereinafter, examples are indicated, but the present invention is not limited to these examples.

Example 1

A silica slurry was obtained, dropping 20% sulfuric acid to 9000 L of a 3.8% sodium silicate solution for 30 minutes with the rate of 21.5 l/minute while applying the shearing force at 95° C., aging it for 90 minutes, simultaneously adding a 9.8% sodium silicate solution with the rate of 38.3 L/minute and 20% sulfuric acid with the rate of 8.3 L/minute to the slurry for 75 minutes, keeping it at 95° C. for 30 minutes, and adjusting the pH to 4 immediately. The obtained silica slurry was filtrated and washed to be adjusted to the about 10% slurry, and it was sprayed and dried using an atomizer type spray dryer made by Ohkawara Kakohki Co. Ltd., to obtain a cyclone collected particles. The obtained cyclone collected particles were baked at 400° C. for 1 hour.

Example 2

After spraying and drying in Example 1, the sample was taken out from a dust collector which was washed and baked at 700° C. for 1 hour.

Comparison Example 1

The cyclone collected particles, which was not baked in Example 1, were used.

Comparison Example 2

The amorphous silica particles in Comparison example 1, which were dried all night at 115° C., were used.

Comparison Example 3

The sample particles, which were not baked in Example 2, were used.

Comparison Example 4

The amorphous silica particles in Comparison example 3, which were dried all night at 115° C., were used.

Comparison Example 5

A commercial Sylysia 350 (made by Fuji Silysia Chemical Ltd.) was used.

Comparison Example 6

A commercial SIPERNAT 50S (made by Degussa Co. Ltd.) was used. Next, the measuring methods of various physical properties are indicated.

Test Example 1

Measuring Method of Oil Absorption

The oil absorption was measured on the basis of JISK 6217-4 (the carbon black for rubber—basic characteristics). The oil absorption according to JISK 6217-4, relates to anhydrous, dried silica. However, in the present invention, the oil absorption relates to moist silica particles (including the loss on drying) obtained after the drying treatment for the commercial circulation was carried out. The intention is to know the properties of the actual usage form.

Test Example 2

Measuring Method of a Nitrogen Adsorption Isotherm

As for the measuring of the nitrogen adsorption isotherm, the adsorption isotherm of nitrogen gas of the sample being vacuum-degassed at 160° C. for 90 minutes was measured by using an automatic specific surface area/pore distribution measuring apparatus BELSORP 28, which was made by Nippon Bel Co. Ltd.

Measuring temperature: −196° C.

Adsorption equilibrium time: 5 minuets

Pore diameter analyzing range (an analyzing method by Dollimore and Heal): 1.0 to 100.0 nm Analyzing of a pore distribution curve The nitrogen adsorption isotherm was measured by the above measuring method, and the pore distribution curve was obtained using adsorbed side data on the basis of JIS-K1150, using the analyzing method by Dollimore and Heal (D. Dollimore, G. R. Heal, J. Appl. Chem., 14.109 (1964)).

Measuring of the pore peak and pore peak radius: In the pore distribution curve, a part showing the maximum value of $\Delta Vp/\Delta \log Rp$ is determined as the pore peak, and the radius at the pore peak is determined as the pore peak radius and indicated in "nm".

Test Example 3

Specific Surface Area Measuring Method (Nitrogen Adsorption Method)

For determining the pore structure of the amorphous silica particles of the invention, the pore peak radius was measured by the nitrogen adsorption isotherm method.

The specific surface area was measured by nitrogen absorption method, the method comprising, vacuum-degassing the sample at 160° C. for 90 minutes, measuring the adsorption isotherm of nitrogen gas of the sample by using the automatic specific surface area/pore distribution measuring apparatus BELSORP 28, which was made by Nippon Bel Co. Ltd., and calculating the specific surface area by BET method. (References: S. Brunauer, P. H. Emmett, E. Teller, J. Amer. Chem. Soc., 60,309 (1938))

Test Example 4

Average Particle Size (Volume Average Size) Measuring Method

The average particle size was measured by selecting the suitable aperture tube and using a multisizer-II made by Coulter Company.

In Table 1, the measuring results of the oil absorptions, the pore peak radius, the specific surface areas and the average particle sizes of Example 1 and 2 and Comparison example 1 to 4 are shown. In FIGS. 1 to 3, the adsorption isotherms of the amorphous silica particles of Example 1 and 2 and Comparison example 1 are shown.

TABLE 1

| Measurement item | Example 1 | Example 2 | Comparison example 1 | Comparison example 2 | Comparison example 3 | Comparison example 4 |
|---|---|---|---|---|---|---|
| Oil absorption (ml/100 g) | 401 | 411 | 343 | 373 | 359 | 375 |
| Pore peak radius (nm) | 82.4 | 44.6 | 29.0 | — | — | — |
| Specific surface area (m2/g) | 178 | 164 | 175 | — | — | — |
| Average particle size (μm) | 5.3 | 3.4 | 5.8 | 5.2 | — | 2.7 |

As a result of the tests, the oil absorption was increased by dehydronizing the sample in Comparison example 1 by drying in Comparison example 2, but the oil absorption was further increased by baking the same sample in Example 1. Further, the oil absorption was increased by dehydronizing the sample in Comparison example 3 by drying in Comparison example 4, but the oil absorption was further increased by baking the same sample in Example 2. As the result, the oil absorptions of Example 1 and 2 were more than 400 ml/100 g.

Test Example 5

Measuring Method of Oil Absorption of Vitamin E

A pipe for dropping the vitamin E, where the hole diameter of the pipe was 1 mm, was mounted to BENCH KNEADER having a 2 L total capacity (made by Irieshokai). Next, about 1 L silica was filled in the kneader, and vitamin E where the viscosity was decreased by heating at 60° C., was dropped to the silica to be oil-absorbed while stirring. For pulverizing the lump generated at the oil absorption, after the oil absorption, the silica was stirred for 30 to 60 seconds with a juicing mixer.

Evaluation method: 2 to 5 g of the vitamin E absorbed particles was taken into a small type pulverizer made by Shibata Science Company (personal mill, SCM-40A type), and was stirred for about 30 seconds. The particle state was observed and the value of the oil absorption, which was just before the appearance of the particles changing from the fine powder to the fine particles or from white to yellow, was determined as the maximum oil absorption. Then, the oil absorption of vitamin E was calculated from the following formula.

Maximum oil absorption=Vitamin E absorption (g)/ Silica weight before absorbing (g)

Results of Test example 5 are given in Table 2:

TABLE 2

| Measurement item | Example 2 | Comparison example 1 | Comparison example 5 | Comparison example 6 |
|---|---|---|---|---|
| Maximum Vitamin E absorption | 3.0 | 2.7 | 2.1 | 2.2 |

As for the absorption of vitamin E, the vitamin E absorption of the amorphous silica particles in Example 2, which was baked, was high as compared with the amorphous silica particles in Comparison examples 1, 5 and 6.

Test Example 6

Measuring Method "Bulk Density"
  The Instrument
1. Stainless steel sieve (Authorized JIS standard sieve) mesh width: 850 micron, diameter: 200 mm
2. Sieve holder(stainless or plastic) side: 250 mm, length: 250 mm, high: 150 mm
3. Receiver(plastic) side: 330 mm, length: 270 mm, depth: 10 mm
4. measurement cup(transparency, plastic) capacity: 100±1 mL, bore: 50.0±10.2 mm, depth: 51.0±0.2 mm, thickness: 5 mm
5. Spatula (plastic) side: 120 cm, length: 40 mm, thickness: 5 mm
6. Spatula (stainless) length: 230 mm The receiver is set. Sieve holder is set upper the receiver. The sieve is set on the sieve holder. The measurement cup known weight is set in the middle of the receiver. The sample is transferred onto the sieve. The sample is dropped with spatula (stainless). (width: 60-70 mm, rate: two times per sec.) The sample is accumulated like conic in measurement cup. The level measurement cup of sample is weighted using a balance.

$$\text{Bulk density} = \frac{S}{100} \quad S\text{: sample weight}$$

Figure 1:
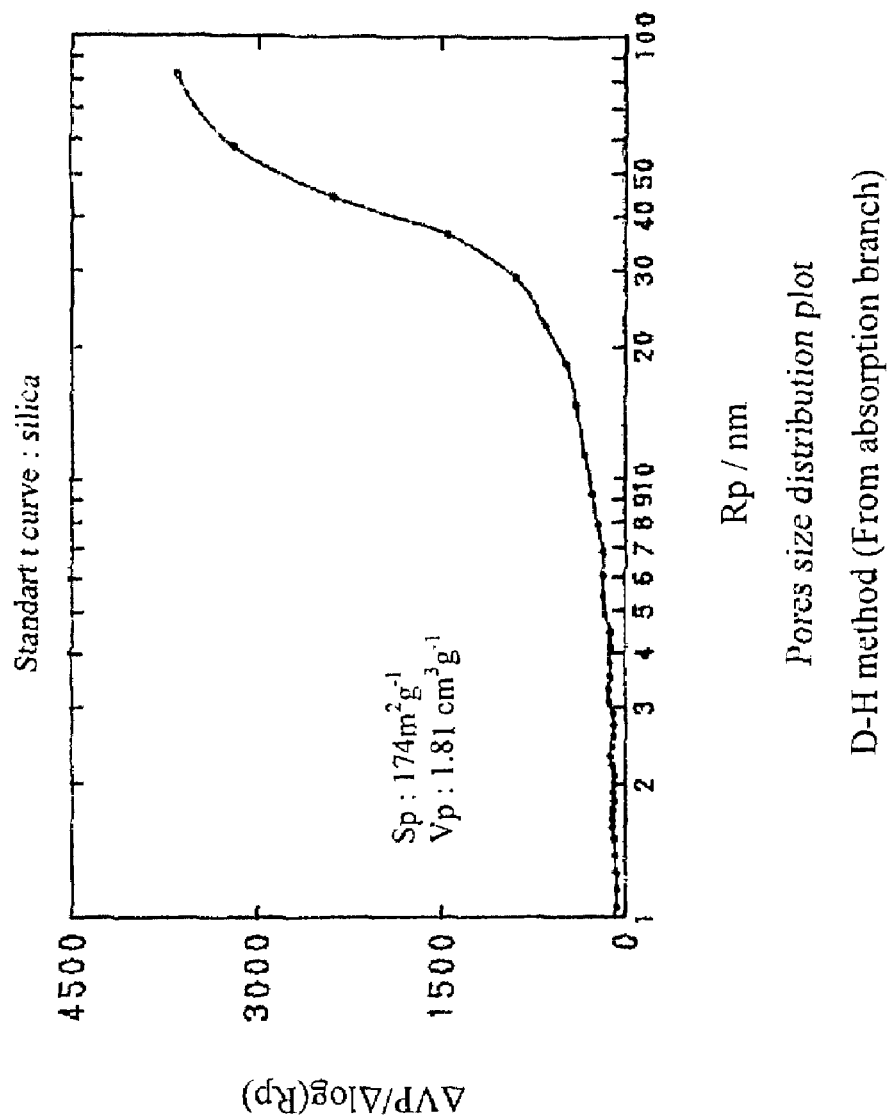
[FIG. 1] A nitrogen adsorption isotherm of the amorphous silica particles in Example 1
Figure 2:
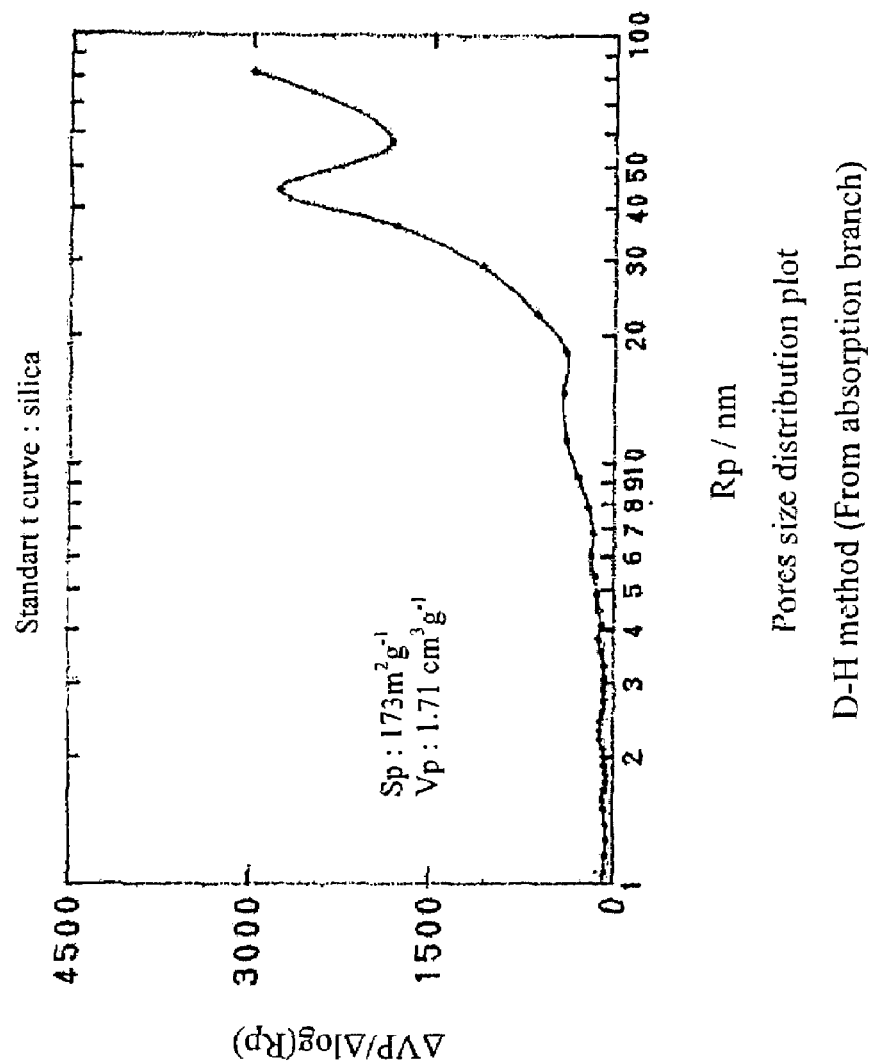
[FIG. 2] A nitrogen adsorption isotherm of an amorphous the silica particles in Example 2
Figure 3:
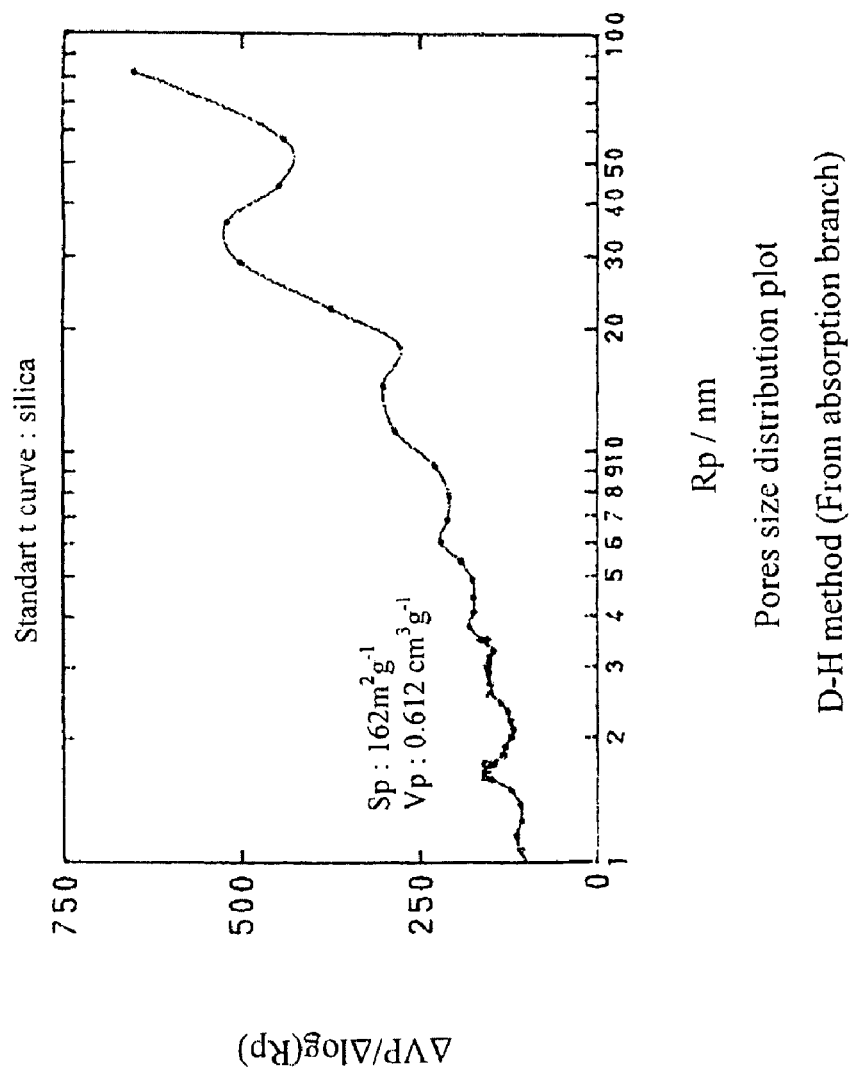
[FIG. 3] A nitrogen adsorption isotherm of the amorphous silica particles in Comparison example 1

The invention claimed is:
1. Amorphous silica particles, wherein
  an oil absorption measured by JISK 6217-4 (a carbon black for rubber-basic characteristics) is more than 400 ml/100 g,
  the maximum value of $\Delta Vp/\Delta \log Rp$ (where Vp is the pore volume [mm$^3$/g] and Rp is the pore radius [nm]) is 250 mm$^3$/nm·g or more in the pore distribution curve obtained by the nitrogen adsorption isotherm method, and
  pore peak radius when the $\Delta Vp/\Delta \log Rp$ value is maximum is 15 to 100 nm.

2. The amorphous silica particles according to claim 1, wherein
the maximum value of $\Delta Vp/\Delta \log Rp$ (where Vp is the pore volume [mm$^3$/g] and Rp is the pore radius [nm]) is 500 mm$^3$/nm·g or more in the pore distribution curve obtained by the nitrogen adsorption isotherm method, and
the pore peak radius when the $\Delta Vp/\Delta \log Rp$ value is maximum is 15 to 100 nm.

3. The amorphous silica particles according to claim 2, wherein
the maximum value of $\Delta Vp/\Delta \log Rp$ (where Vp is the pore volume [mm$^3$/g] and Rp is the pore radius [nm]) is 1000 mm$^3$/nm·g or more in the pore distribution curve obtained by the nitrogen adsorption isotherm method, and
the pore peak radius when the $\Delta Vp/\Delta \log Rp$ value is maximum is 15 to 100 nm.

4. The amorphous silica particles according to claim 1, wherein the maximum value of $\Delta Vp/\Delta \log Rp$ (where Vp is the pore volume [mm$^3$/g] and Rp is the pore radius [nm]) is 2500 mm$^3$/nm·g or more in the pore distribution curve obtained by the nitrogen adsorption isotherm method.

5. The amorphous silica particles according to claim 1, wherein the average particle size is 0.5 to 40 µm.

6. The amorphous silica particles according to claim 1, wherein the bulk density is 20 to 200 g/l.

7. The amorphous silica particles according to claim 1, obtained by baking.

8. A process for preparing amorphous silica particles according to claim 1, the process comprising
baking silica particles having an oil absorption of at least 340 ml/100 g at 200-990° C. for 1 minute to 10 hours.

9. The process as claimed in claim 8, wherein the time for baking is 10 minutes to 5 hours.

10. The process as claimed in claim 8, wherein the resulting amorphous silica exhibits an oil absorption of more than 400 ml/100 g.

11. The process as claimed in claim 8, further comprising the step of reacting at least one alkali metal silicate with at least one mineral acid.

12. The process as claimed in claim 11, further comprising the step of adjusting the pH value of the final silica to 3 to 10 either before or after the drying of the silica slurry.

13. A method of using a silica, the method comprising mixing the amorphous silica particles of claim 1
in a coating material as a matting agent, or
in pharmaceuticals or agrochemicals as a carrier, or
in a rubber as a reinforcing agent.

14. An adsorbent for pharmaceuticals, agrochemicals, comprising the amorphous silica particles of claim 1.

15. A matting agent, comprising the amorphous silica particles of claim 1.

* * * * *